(12) United States Patent
Liu

(10) Patent No.: US 8,772,744 B1
(45) Date of Patent: Jul. 8, 2014

(54) AIR-FLOW ACTIVATED GERMICIDAL UV-C LIGHTS IN HVAC SYSTEM

(71) Applicant: Benjamin Dengfa Liu, Carmel, IN (US)

(72) Inventor: Benjamin Dengfa Liu, Carmel, IN (US)

( * ) Notice: Subject to any disclaimer, the term of this patent is extended or adjusted under 35 U.S.C. 154(b) by 0 days.

(21) Appl. No.: 13/752,499

(22) Filed: Jan. 29, 2013

(51) Int. Cl.
*G01F 1/06* (2006.01)
*G01F 3/00* (2006.01)

(52) U.S. Cl.
USPC ............... 250/504 R; 250/365; 73/204.23; 73/53.04; 422/121; 700/276

(58) Field of Classification Search
USPC ............... 700/276; 422/121; 250/504 R, 365; 73/204.23, 53.04
See application file for complete search history.

(56) References Cited

U.S. PATENT DOCUMENTS

| 6,543,282 B1 * | 4/2003 | Thompson ................. 73/204.15 |
| 7,653,459 B2 * | 1/2010 | Pouchak et al. ............. 700/276 |
| 2002/0176809 A1 * | 11/2002 | Siess ........................... 422/121 |

* cited by examiner

*Primary Examiner* — Nikita Wells

(57) ABSTRACT

UV-C light assembly is designed to kill germs (bacteria, molds, protozoa, virus, and yeast) in the forced airstreams of HVAC systems, thus preventing the spreading of germs into other rooms or spaces. An air-flow activated switch is invented for turning on the UV-C lights when airstreams pass through and turning off when airstreams stop in the HVAC systems. The UV-C light assembly is installed inside duct through air filter's opening. The UV-C germicidal assembly is an easy add-on to an existing HVAC system for indoor air purification. The UV-C light sources are either LEDs or fluorescent tubes.

10 Claims, 3 Drawing Sheets

A Structure of air-flow activated UV-C light Assembly

Figure 1: A Structure of air-flow activated UV-C light Assembly
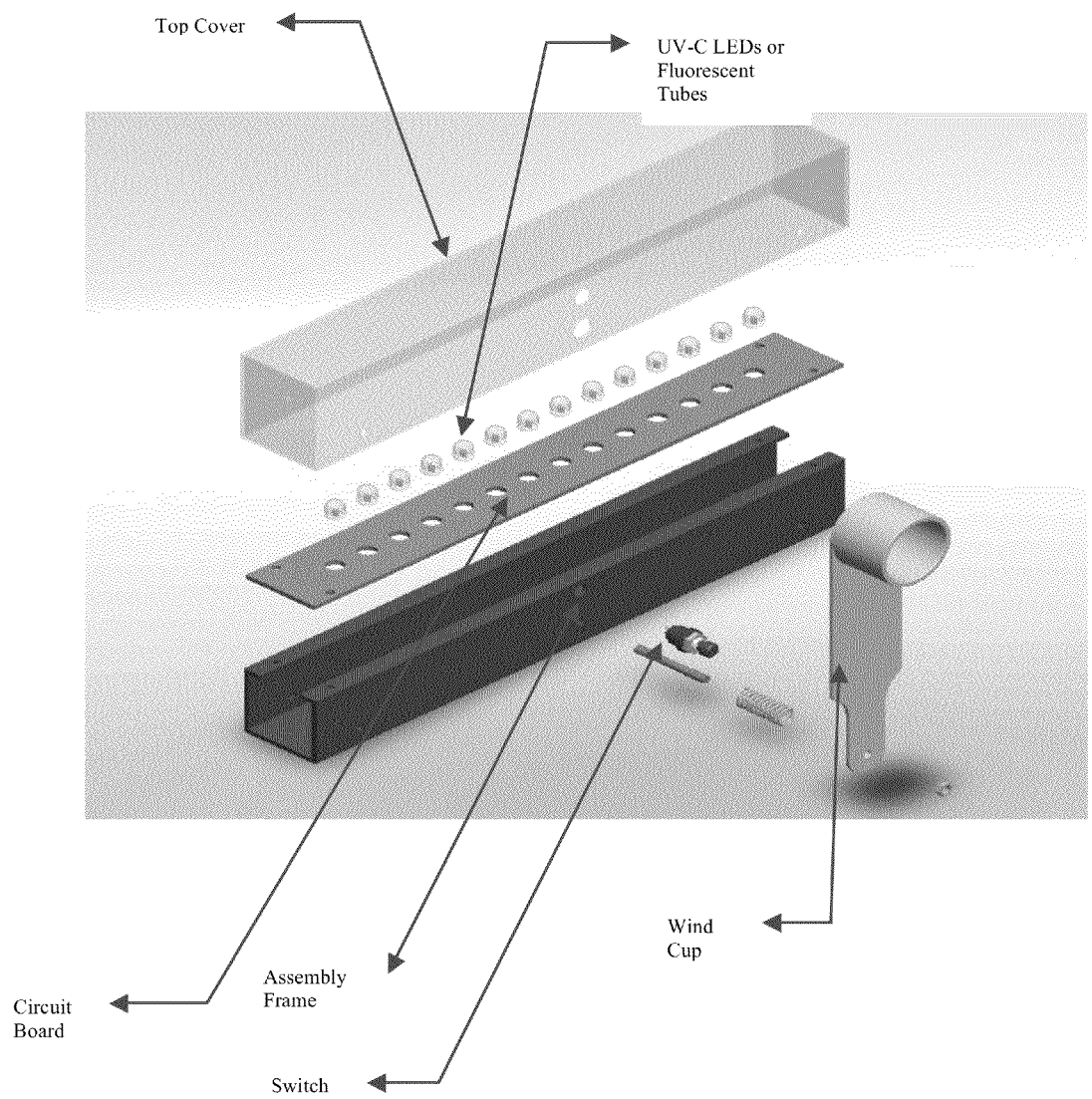

Figure 2: An assembled unit of air-flow activated UV-C light Assembly
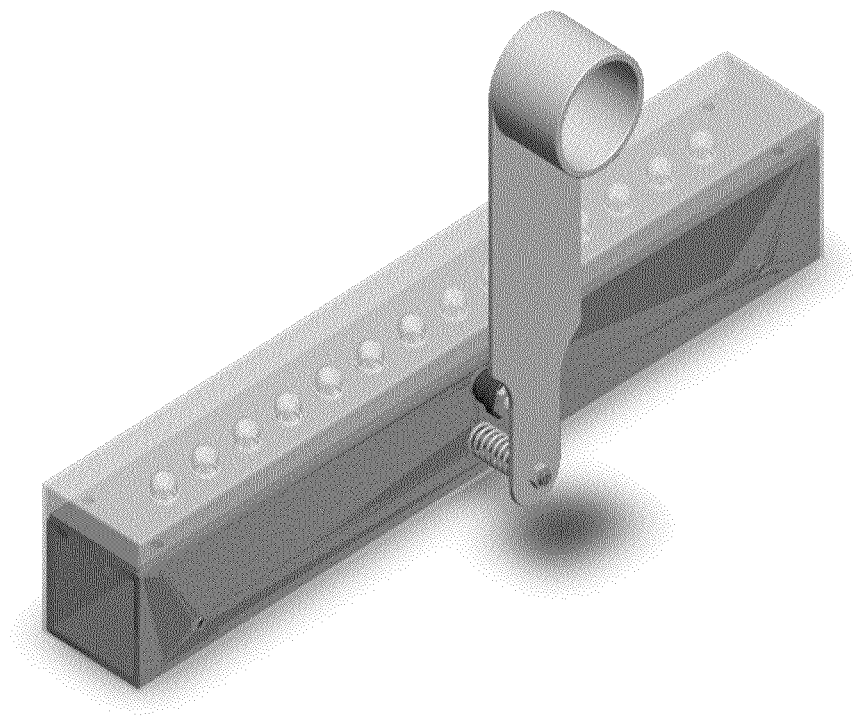

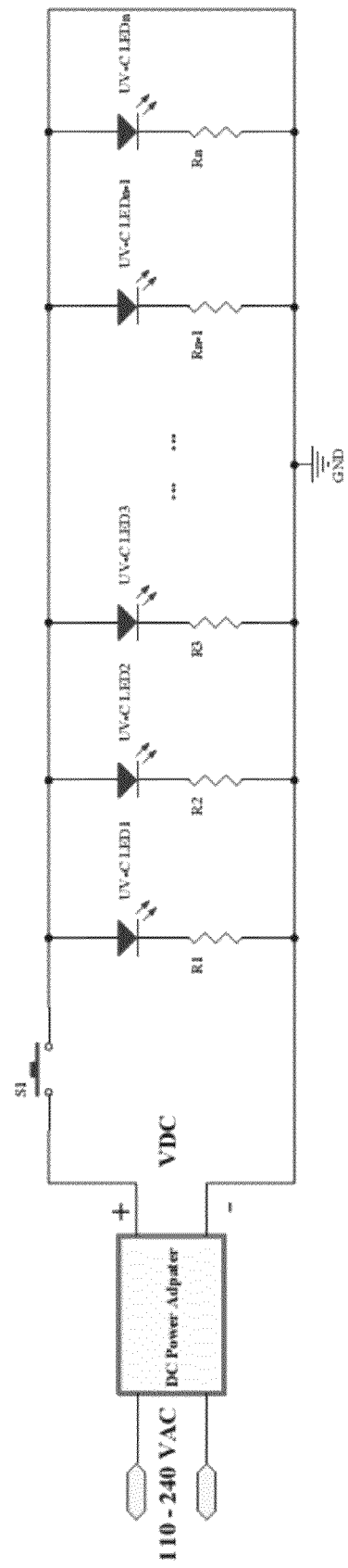
Figure 3: An illustration of a typical LED circuit. AC is converted to DC current to supply the required power to n sets of UV-C LEDs and resistors. S1 is a push-to-make momentary switch.

AIR-FLOW ACTIVATED GERMICIDAL UV-C LIGHTS IN HVAC SYSTEM

BACKGROUND OF THE INVENTION

It is well known that sunlight purifies air. More specifically, it is the light in the UV-C wavelength range (around 260 nm) that purifies air. UV-C light is germicidal by deactivating the DNA of viruses, bacteria, and dust mites. However, this natural germicidal process doesn't occur indoors. Many UV-C germicidal systems have been invented for indoor uses such as UV-C sanitizing wands, UV-C housing used inside HVAC systems, and etc.

SUMMARY OF THE INVENTION

This invention designed an UV-C light assembly for air purification inside HVAC systems.

We use light-emitting diodes (LEDs) or fluorescent light tubes in the wavelength range of UV-C centered at about 260 nm. The UV-C wavelength is peaked at 260 nm with 10 nm of FWHM. The light assembly is placed inside air duct of a HVAC system. When the HVAC system starts to work, the fan drives the air in the duct to flow. The airstream pushes the air cup to press on the switch, and thus causing the switch to close to power up the LEDs or the fluorescent tubes. The UV-C light purifies the air that flow through the light. When the fan stops, the air cup stops pressing the switch and the UV-C light assembly shuts off.

The UV-C light assembly is designed in such a way that it can be fitted through the openings of air filters.

This UV-C light assembly is suitable for any central HVAC systems.

BRIEF DESCRIPTION OF THE DRAWINGS OF THE INVENTION

FIG. 1 is a structure of air-flow activated UV-C light assembly.

FIG. 2 is an assembled unit of air-flow activated UV-C light assembly.

FIG. 3 is an illustration of a typical LED circuit.

DETAILED DESCRIPTION OF THE INVENTION

1. The Physical Structure
The invented UV-C light assembly consists of units as follows:
(a) Assembly Frame (FIG. 1)
   A frame that can be made of metal or plastics holds all other parts together to form the assembly.
(b) Circuit Board (FIG. 1)
   The circuit is etched on the board with necessary electronic components and LEDs welded (or fluorescent tubes are installed).
(c) Wind Cup (FIG. 1)
   The wind cup is designed to catch the air that flows in the duct. A spring system is used to hold the wind cup.
(d) Switch (FIG. 1)
   The switch is a push-to-make momentary switch, meaning the switch closes when the button is pressed down.
(e) Assembly Cover (FIG. 1)
   The cover protects its components from any possible harm in the air duct environments.

2. Operation of Air-Flow Activated Germicidal UV-C Light Assembly
Air-flow activated germicidal UV-C light assembly (light assembly) is designed to be used with central HVAC systems. The UV-C light assembly is installed inside air ducts. When air flows, the light assembly turns on. When air flow stops, the light assembly turns off. When the light assembly turns on, it emits UV-C light and illuminates a section of the duct. Air flowing through this light illuminated section is purified by UV-C light. Here is how this light assembly works:
(a) LEDs (or fluorescent UV-C tubes) are installed on the circuit board according to FIG. 3. When the switch turns on, the LEDs emit UV-C light.
(b) If the air in the duct doesn't flow, meaning the HVAC system is off, the wind cup stands up and not in touch with the switch.
(c) If the air in the duct flows, meaning the HVAC system is on, the wind cup is being pushed toward the switch. The push from the wind cup turns the switch on. When the switch is on, the LEDs (or the fluorescent tubes) emit UV-C light.
(d) While the light assembly is on, the air flows through the illuminated section. The UV-C light purifies the airstream.

CROSS-REFERENCES FOR THE INVENTION OF AIR-FLOW ACTIVATED GERMICIDAL UV-C LIGHT ASSEMBLY

U.S. Pat. No. 7,976,195 Engel, et al
   An UVC lamp and reflector/shield assembly is designed to be used in a commercial HVAC unit. The reflector in the assembly creates an illuminating pattern. The outer surface of the assembly provides shielding for the UVC lamp from the air flow.
U.S. Pat. No. 8,004,166 Boehme
   The author designed a mercury based UVC lamp that prevents the formation of a cold spot in the lamp.
U.S. Pat. No. 8,252,099 and U.S. Pat. No. 8,252,100 Worrilow
   An air purifier is designed that includes a housing with an inlet for receiving air and an outlet for exhausting air. The housing has a particle pre-filtration, UV filtration, and volatile organic compound post filtration. This purifier is intended to use in research laboratories.
U.S. Pat. No. 7,837,933 Sevack, et al
   This patent is similar to U.S. Pat. No. 7,976,195
U.S. Pat. No. 7,740,686 Metteer
   A modular ductwork assembly decontaminates an air stream circulating with a HVAC system. The assembly includes an ionizing module, sterilization module, ozone treatment module. The sterilization module uses UVC light.
U.S. Pat. No. 7,278,272 Huston, et al
   A germicidal UVC lamp is mounted near evaporator coil in a HVAC system to sterilize the air and surfaces of the coil.
U.S. Pat. No. 7,175,814 Dionisio
   A cartridge device containing UVC for air disinfection comprises individual UV bulb, filter, ballast and electrical components.

The invention claimed is:
1. An air-flow activated germicidal UV-C light fixture comprising a UV-C light source, an air-flow catching wind cup serving as an air-flow sensor and switch trigger on one end of a lever and NOPB (Normally Open Push Button Switch) on the other end, wherein air-flow pushes the wind cup to force the other end of the lever to press down the NOPB, and thus to close the electrical circuit and results in the turning on of the UV-C light, and then the UV-C light and the switch are mounted to the circuit housing, which is installed to a HVAC system.

2. The said air-flow sensor of claim 1 further comprising a heating element and a temperature sensing thermal couple at a tip, a microcontroller, a relay drive circuit, a relay, an electricity power cord, a circuit housing, and a mounting device, wherein air-flow quenches the tip's temperature and the microcontroller senses the drop of the temperature through the thermal couple and thus the presence of the air flow, and the microcontroller turns on the relay drive circuit and relay, and thus the UV-C light.

3. The said air-flow sensor of claim 1 further comprising a heating element and a temperature sensing thermistor at a tip, a microcontroller, a relay drive circuit, a relay, an electricity power cord, a circuit housing, and a mounting device, wherein air-flow quenches the tip's temperature and the microcontroller senses the drop of the temperature through the thermistor and thus the presence of the air flow, and the microcontroller turns on the relay drive circuit and relay, and thus the UV-C light.

4. The said air-flow sensor of claim 1 further comprising a wind triggered movement device and a proximity sensor, wherein the proximity sensor senses the movement of the wind-triggered device and thus the presence of the air flow, and the microcontroller turns on the relay drive circuit and relay, and thus the UV-C light.

5. The said air-flow sensor of claim 4 further comprising a moveable part, wherein the moveable part moves with the air flow and set into an air-flow position, and returns to its original position when there is no air flow presents.

6. The said air-flow sensor of claim 4 further comprising a photo electric sensor and a weak infrared LED beam, wherein the moveable device of claim 5 is triggered into the air-flow position in such a way that it affects the passage of the infrared LED beam, and thus sets the photo electric sensor into the state of turning on the relay.

7. The said air-flow sensor of claim 4 further comprising a magnetic field sensor and metallic trigger device of claim 5, wherein the metallic moveable device is set into the air-flow position, the magnetic field sensor sees the change in the electromagnetic field and turns on the relay.

8. The said air-flow sensor of claim 4 further comprising a capacitive sensor and a plastic air-flow triggered movement device of claim 5, wherein the plastic moveable device is set into the air-flow position, the capacitive sensor sees the change in the capacitance and turns on the relay.

9. The said air-flow sensor of claim 4 further comprising an ultrasonic sensor and an air-flow triggered movement device of claim 5, wherein the moveable device is set into the air-flow position, the capacitive sensor sees the change in the capacitance and turns on the relay.

10. According to claim 4, an air-flow sensor turns on the UV-C light assembly when the air flows inside the HVAC duct; the switch turns off the UV-C light assembly when the air doesn't flow inside the HVAC duct; the UV-C light illuminates a section of HVAC duct; and the UV-C light purifies air stream that passes by the section by killing the viruses, bacteria, and dust mites.

* * * * *